United States Patent [19]

Bitterly

[11] Patent Number: 4,569,355

[45] Date of Patent: Feb. 11, 1986

[54] METHOD AND APPARATUS FOR MONITORING AND DIAGNOSING PERIPHERAL BLOOD FLOW

[75] Inventor: Jack G. Bitterly, Woodland Hills, Calif.

[73] Assignee: Hemodynamics Technology, Inc., Newbury Park, Calif.

[21] Appl. No.: 383,004

[22] Filed: May 28, 1982

[51] Int. Cl.4 .............................................. A61B 5/02
[52] U.S. Cl. .................................... 128/691; 128/399
[58] Field of Search ................ 128/691, 736, 399–400, 128/402–403; 73/204; 165/34; 62/63, 527

[56] References Cited

U.S. PATENT DOCUMENTS

| Re. 30,317 | 7/1980 | Lübbers | 128/635 |
|---|---|---|---|
| 2,551,650 | 5/1951 | Urbach | 250/337 |
| 2,982,132 | 5/1961 | Mendlowitz | 128/691 |
| 3,479,838 | 11/1969 | Bitterly | 62/259.3 |
| 4,175,543 | 11/1979 | Suzuki | 128/736 |
| 4,191,197 | 3/1980 | Benzinger | 128/736 |
| 4,228,805 | 10/1980 | Rosen | 128/691 |

Primary Examiner—Lee S. Cohen
Assistant Examiner—Angela D. Sykes
Attorney, Agent, or Firm—Koppel & Harris

[57] ABSTRACT

A heat exchanger changes the temperature of a predetermined area of the skin at a programmed rate preferably by cooling. The rate at which the area of skin changes in response to temperature change of the heat exchanger and the rate the skin temperature returns to normal are then measured and compared to standard rates over a number of cycles. Impaired peripheral blood flow is evident especially on subsequent cycles as vascular disease slows the rate of return to normal temperature of the skin. The heat exchanger has a cooling chamber with one side of the chamber being a cooling surface adjacent to the skin. An injector is connected to a source of fluid having a boiling point at ambient pressure less than the temperature to which the skin is to be cooled and greater than ambient temperature of the apparatus. The injector injects fluid into the chamber and onto the side of the cooling surface opposite the skin to boil the fluid on the surface to cool the surface and the skin.

36 Claims, 7 Drawing Figures

METHOD AND APPARATUS FOR MONITORING AND DIAGNOSING PERIPHERAL BLOOD FLOW

BACKGROUND OF THE INVENTION

This invention relates to a method and apparatus for monitoring and diagnosing peripheral vascular blood flow in people or animals. Part of the apparatus uses a novel heat exchanger.

Peripheral vascular disease ("PVD") is defined as impaired arterial or venous blood circulation. More than one percent of the United States population has some form of PVD.

PVD may take many different forms, but it usually affects the leg, especially the femoral and popliteal (thigh and knee) regions. A major cause of venous PVD is deep vein thrombosis. Arteriosclerosis, which occurs more frequently with increased age, is usually progressive is a major cause of PVD in the arteries. Approximately forty percent of PVD cases are a result of complications from diabetes.

As PVD becomes more advanced, blood flow can be so limited that tissues will die, which leads to gangrene. As a result amputation is required above the gangreneous tissue. Cramps, charlie-horse or calf or thigh discomfort during leg movement are symptoms of milder PVD. Pain and the other symptoms increase as PVD becomes more advanced.

There are a number of methods for diagnosing PVD, but no simple screening devices for evaluating PVD accurately are now available. A number of the diagnostic techniques involve invasive diagnosis in which veins or arteries are entered by needles or catheters. In arteriography, after a contrast dye is injected into the arteries, the arteries are viewed using X-rays. Arteriography provides a detailed image of the arterial system, and it is the accepted standard for evaluation of an arterial disease before operations. Arteriography is expensive, and there is an element of risk, discomfort and exposure to radiation. Venography is similar to arteriography except the procedure is applied to veins. Both arteriography and venography are in widespread use but they cannot be used as a simple screening test for PVD.

There are also certain non-invasive tests for PVD in which the veins and arteries are not entered and are not exposed to X-ray examination. Non-invasive techniques have substantially less risks to the patient but they require skilled technicians and are usually limited to hospital settings. The non-invasive procedures now in use include segmental plethysmography, doppler ultrasound pulse analysis, electrical impedance measuring devices and a less-invasive arteriography called digital subtraction angiography. Segmental plethysmography measures blood volume in a limb or changes in blood pressure at different positions on the extremity such as at the thigh, calf, ankle and foot. A pulse volume recorder records arterial wave forms at each location. PVD in an artery alters the wave forms. As arteriosclerosis progresses, however, plethysmography becomes progressively less accurate. Therefore, an additional wave form analysis is performed on data provided by a doppler ultrasound instrument. As is well known, moving bodies shift the frequency of sound reflected from them. Doppler measuring instruments measure the difference between the frequency of transmitted sound and that of the reflected sound, and the difference is proportional to the velocity of the moving bodies. Red blood cells are such moving bodies, and their movement have been measured using doppler measurements. Plethysmography combined with doppler ultrasound measurements have provided a moderately accurate assessment of arterial PVD with less expense and lower risk than invasive techniques. Arteriography is still needed if surgery is contemplated. Plethysmography and doppler methods also measure the relative blood volume in a limb at a given time, and they are useful in evaluating deep vein thrombosis.

Electrical impedance measuring devices have also been used to diagnose PVD. These devices operate on the principle that a decrease in the electrical resistance of a limb is directly proportional to the increase in the blood volume. Because of a relatively high occurrence of false, positive results, clinical use of these devices is declining.

Although digital subtraction angiography is not invasive in that it does not require catheterization of the arteries, it does use radiation and the injection of a radiopaque tracer dye. A computer "subtracts" the X-ray picture after the dye is in the arteries from an X-ray taken before the dye is injected. Although this system is accurate, there is still a need for a simplified, non-invasive PVD diagnostic technique that involves no radiation or injection.

It is most important that the extent of PVD be diagnosed accurately and timely. In order to prevent gangrene, if PVD cannot otherwise be treated, amputation is frequently required. Obviously, the drastic step of amputation should not be undertaken unless PVD has progressed sufficiently. Therefore, false positive tests, giving incorrect evidence requiring amputation, should be avoided. The failure of a test to yield positive results when truly indicated is also a problem in that PVD can be life threatening. Once PVD is detected, preventative treatment can be timely started to avoid or delay amputation.

Once PVD has progressed beyond the stage that it can be treated to the point that amputation is required, a surgeon must decide where on the leg to amputate. If the amputation is done too low, PVD prevents sufficient blood flow to heal the amputation wound. If the amputation is too high, larger and more complicated prostheses will be necessary. This is especially true in deciding whether to amputate above or below the knee. Therefore, it is important to be able to determine the extent of PVD and its location.

With the exception of simple blood pressure testing and some doppler applications, the systems and methods discussed are performed in a hospital. This substantially increases their expense and decreases their general availability. What is desirable, therefore, is a simple, reliable and accurate test to measure vascular circulation in a physician's office (or even in a patient's home) both for initial screening and subsequent evaluations of PVD.

It is known that changes in the skin temperature of an extremity may indicate the presence or absence of blood flow. Heat transfer from the blood in the subcutaneous capillary bed to the skin is a function of the increase or decrease in blood supply from the arteries and the rate with which the blood is emptied from the capillary system by the venous system. Although factors such as muscle tone, activity, posture, venimotor tone, disease, reflexes and drugs affect cardiovascular function and blood flow, these affects can be minimized by environmental controls. Skin thermodynamics is therefore related to cardiovascular function insofar as cardiovascular function affects peripheral and capillary blood flow. Obstructions or occlusions in the peripheral vascular system will have a direct, measurable affect on heat transfer at the skin's surface.

The present invention may also have application in diagnosing all diseases that affect skin temperature and that now are diagnosed using infrared scanning.

SUMMARY OF THE INVENTION

The method of the present invention first applies an object which changes temperature to a predetermined area of the skin at a programmed rate. The rate at which the area of skin changes in response to temperature change of the object and the rate the skin temperature returns to normal, are then measured, and one compares the rates to standard rates. One may also lower the frequency during subsequent cycles of the same test. The rates and frequencies are functions of blood flow.

Although the skin temperature could be changed by heating the area (see U.S. Pat. No. 4,228,805 to Rosen (1980)), the present invention uses cooling. Cooling is accomplished by means of a small heat exchanger mounted on a cuff attached at or around an extremity. The heat exchanger has a unique system that injects a liquid into a chamber. The liquid boils from skin temperature heat energy at atmospheric pressure and cools the surface of the chamber that contacts the skin, thus cooling the skin. In the preferred method, the heat exchanger is quickly lowered to a pre-set minimum temperature. The skin temperature quickly drops, and then the heat exchanger is turned off, either in response to skin temperature measurements, after a certain predetermined time, and/or in response to a predetermined heat flux being applied to the skin. The skin temperature begins to rise back to its normal temperature. A second cycle is initiated after a predetermined off time and/or after the skin temperature reaches its normal temperature. The heat exchanger is again activated for a second cycle. On subsequent cycles, there is usually, even in normal individuals, an increase in the time necessary to return the skin temperature to normal.

After a given number of cycles one can view and compare to normal a graph of the temperature-versestime chart. In persons with PVD, the rate at which skin temperature drops and returns to normal will change, and each cycle will yield a greater change. One who is experienced in comparing the graph can evaluate them for the presence or absence of PVD. Moreover, the curves can be analyzed mathematically to yield a number that could be non-dimensional and that changes to reflect the normalcy of the capillary bed at the point of measurement. These numbers can be compared to standards for so-called normal persons of given age, sex, height and weight for an indication of disease.

The principal object of the present invention is to disclose and provide a new and improved vascular monitoring system for diagnosing PVD safely, accurately and at low cost. To accomplish the principal object, the invention has a further object to be non-invasive and produce a minimal affect on vascular functions during monitoring. Another object is to provide equipment for vascular monitoring that can be manufactured at relatively low cost and will utilize low power outputs for patient safety. Although the test results can be displayed by analog means or printed alpha-numerically in a form that requires training to understand, a further object of the invention is to provide a readout that can be understood by those of lesser training. A further object is to have the system sufficiently simply so that it can be used to monitor a patient's vascular function by relatively unskilled persons.

Other objects relate to the ability for regular use of the system to note PVD changes-good or bad. It is an object to construct a vascular monitoring system that can be used regularly for monitoring patients already believed to have PVD and for monitoring patients recovering from vascular surgery.

There are many ways in which the skin could be cooled, but a desirable cooling system should have certain properties. Only a small area of the skin normally must be cooled. Therefore, a large heat exchanger is not necessary. If the size can be sufficiently reduced, PVD can be monitored in such extremities as the toes and fingers. It may be possibly advantageous to attach larger heat exchangers to cover a major area of the body such as the entire lower leg. For accurate measurement, the rate of cooling of the heat exchanger must be exact, and the timing of the heat exchanger must be precisely controlled. If not, the skin will be reduced in temperature too slowly, too fast or to an incorrect temperature for readings to be compared accurately with "normal" or later test results. Another problem is in the control of the heat exchanger. The lag time from which start or stop commands are initiated should be minimized. It is therefore an object of the present invention to minimize the lag time. Another problem is in the controlling of the heat exchanger. One of the most efficient heat exchangers is one in which a phase change takes place. As was discussed in U.S. Pat. No. 3,479,838 (1969) to J. G. Bitterly, the skin body heat can cause certain liquids to vaporize, which cools the skin. It is possible to choose a liquid that can be vaporized at skin temperature but will not vaporize in normal room temperature assuming normal atmospheric pressure. The liquid can be applied to the opposite side of a surface that is attached to and heated by the skin. The heat energy from the skin vaporizes the liquid to cool the surface and the skin by means of the latent heat of vaporization. The vapor contains the heat energy given off by the skin and ejects it to the ambient atmosphere.

One of the potential problems with such a system is in controlling the liquid flow on to the vaporizing surface. As the liquid must be stored under pressure, relatively large valves would be needed to control the flow of liquid. If these valves are electrically controlled, however, large amounts of electrical power will have to be fed to the heat exchanger mechanism on the patient's skin. This is dangerous in that a short could develop after extended use. One of the objects, therefore, of the present invention is to utilize the pressurized liquid itself in controlling the flow of liquid. The present invention utilizes a hydraulic amplifier that requires only minute amounts of electrical energy for controlling low pressure liquid or gas, and the low pressure liquid or gas then controls the higher pressure liquid. This permits a portable and power independent miniaturized system that can be stored in a small case similar to those that store calculators.

Another object of the present invention is to ensure that the heat exchanger is reliable and will yield the same heat flux each time the heat exchanger is activated.

These and other features will become evident from the detailed description of the invention that follows.

DETAILED DESCRIPTION OF THE PREFERRED EMBODIMENT

When a cold or warm object is applied to an area of the skin, the rate at which the skin cools or warms and at which the body returns that portion of skin to its normal temperature can be correlated to the efficiency of the vascular supply system. Therefore, the present invention relies upon the principle that skin thermodynamics is related to peripheral blood flow which in turn is related to cardiovascular function.

Figure 5:
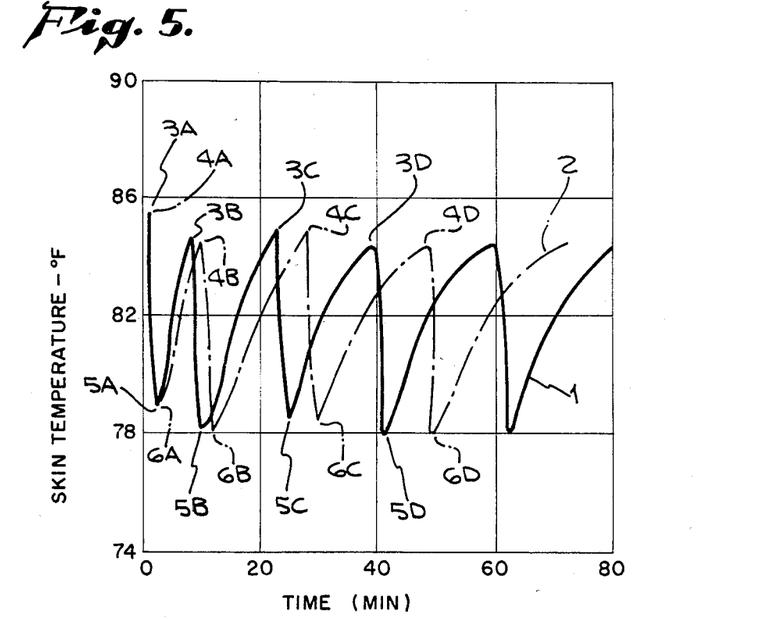
FIG. 5 is a graph showing skin temperature changes over time for two patients being monitored by the present invention.

It has also been discovered that by applying cooling to the same area of skin after the skin temperature recovers to normal after a previous application of cooling, the second return to normal will take longer. (Cooling is used in the preferred embodiment for reasons set forth below.) As this process is repeated, the length of time for recovery will continue to increase. This is best illustrated in FIG. 5 in which skin temperature is plotted against time. Although the exact skin temperature versus time curves may change depending on various factors, curve 1 is representative of the temperature versus time curve for an adult male suffering no PVD. Curve 2, superimposed in FIG. 5, on the other hand, is a hypothetical curve for the same size male suffering some PVD. The present invention offers a safe and inexpensive way of obtaining various curves. Because thermodynamics of the skin accurately and reproducibly reflect aspects of a person's vascular condition, by comparing curves 1 and 2, the person's vascular condition can be observed under controlled, and yet somewhat variable, conditions without introducing significant measuring artifacts.

Cooling rather than heating is used for a number of reasons. First, persons are accustomed to having their skin exposed to relatively cold surfaces down to approximately 50° F. (10° C.). The same temperature change applied as an increase temperature to the skin could be painful or at least uncomfortable. The other reason for using cooling is because the vapor phase-change heat exchanger of the present invention can cool very quickly and with absolute safety. As will be explained below, cooling can be done by a small, lightweight and accurate device.

The cooling cuff 30 (FIGS. 1 and 2) is attached to the calf portion 11 of the patient's leg 12 by one or more straps 126 (two are used in the exemplary embodiment) connected at their ends by Velcro fasteners 127. Because the heat exchanger and monitors are small, the cuff could be designed small enough to attach to a finger or toe.

Figures 1, 2, 3:
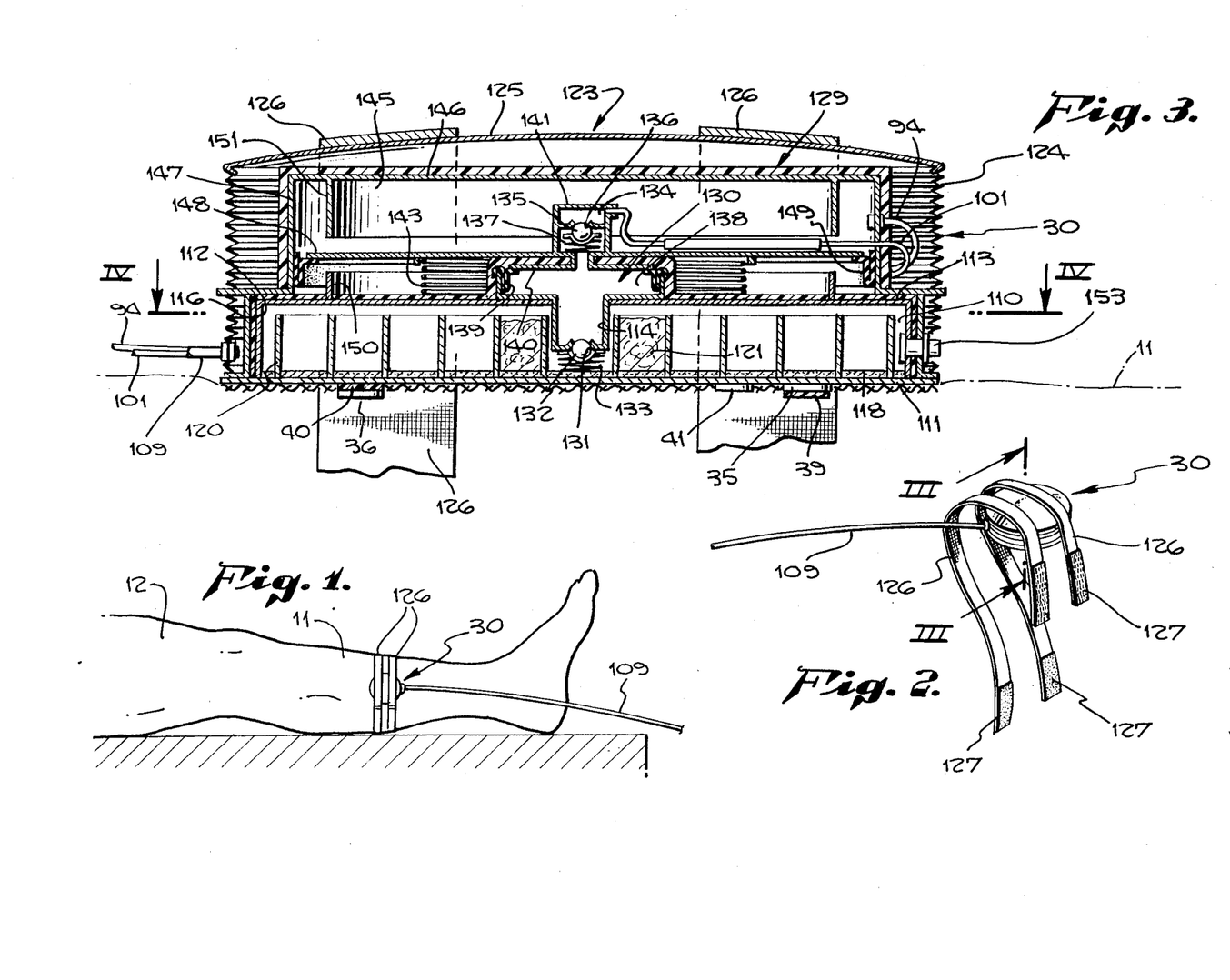
FIG. 1 is a side elevation of the cooling cuff, which contains the heat exchanger of the present invention. The cuff is shown on a patient's leg.
FIG. 2 is a perspective view of the cuff which shows the heat exchanger.
FIG. 3 is a sectional elevation of the heat exchanger that is attached to the patient's extremity.
Figure 4:
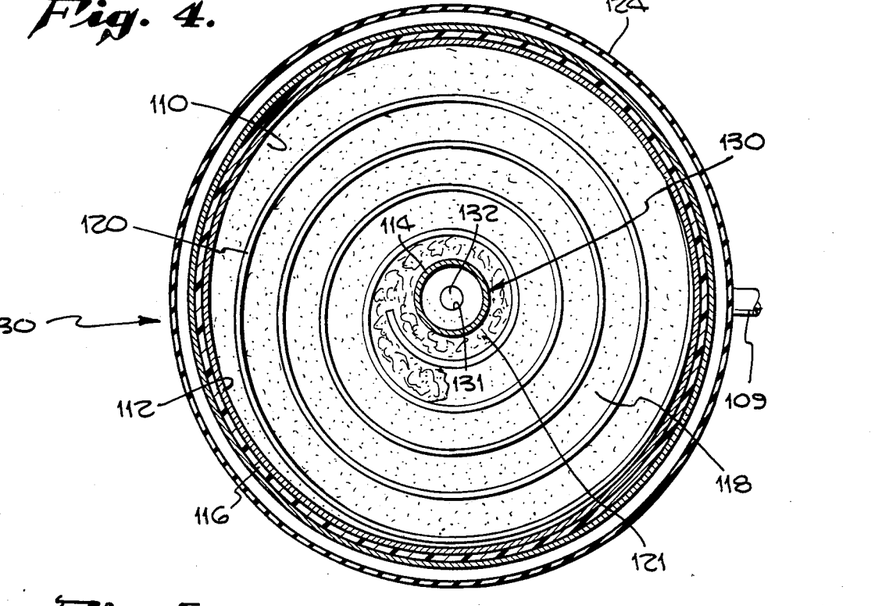
FIG. 4 is a plan sectional view of the heat exchanger taken through plane IV—IV in FIG. 3.

Although cooling could be accomplished in a number of ways, the preferred exemplary embodiment utilizes the heat exchanger of the present invention. The details of the heat exchanger are shown in FIGS. 3 and 4, and the schematic operation is shown in part in FIG. 7. The heat exchanger of the present apparatus comprises a cooling chamber 110 which is formed from a bottom heat exchanger surface 111, a cylindrical sidewall 112 and a top wall 113. Part of injector 130 extends downward through opening 114 in top wall 113. The sidewall 112 and top wall 113 are covered with insulation 116 to limit heat transfer from the outside through those walls into the chamber. Cooling surface 111 should be formed of a high heat transmitting material. Gold and silver offer the best heat transmission, but copper or aluminum may be acceptable alternatives especially if plated with a protective, noncorroding layer of gold because of the lower cost of these metals. Cooling surface 111 may be flat, or it may be curved to accommodate the particular appendage being monitored. A flat surface would work relatively well when attached to the leg or arm, but a curved surface would yield better surface skin contact on a finger or toe.

Injecting means, which is connected to a source of pressurized liquid having a boiling point at atmospheric pressure less than the temperature to which the skin is to be cooled, injects the liquid into chamber 110 against surface 111. The heat transmitted from the body through surface 111 heats the liquid to cause it to boil at atmospheric pressure. The phase change from liquid to gas extracts heat from surface 111 which in turn extracts heat from the skin thereby cooling the skin. Although the injecting means 130 will be described in further detail below, liquid under pressure will be injected through orifice 131 (FIG. 3) which is sealed by check ball valve 132 which is biased against the orifice by spring 133. As the liquid is injected through orifice 131, it should contact surface 111.

To facilitate distribution of the liquid radially outward along surface 111, a wick 118 is provided on the surface to cause the liquid to flow along the entire surface. Wick 118 may be any wicking materials such as fibers, porous stones or screens. A wick may also surround spring 133 to transport the liquid to surface 111 and wick 118. In case the heat exchanger is not oriented with cooling surface 111 horizontal, guide means on the surface are provided for transporting the fluid from the injecting means to spaced apart locations on the surface means. In the exemplary embodiment, the guide means comprises a spiral wall 120 (FIGS. 3 and 4). The fluid that is injected into the chamber cannot, therefore, immediately fall to one location on sidewall 112. A secondary wick 121 in the form of a fabric or other wicking material in the first winding or two of the spiral directs fluid to the primary wick 118 when the unit is not mounted horizontally. Thereafter, the primary wick 118 will draw fluid along the spiral 120 so that it is exposed to heat transfer surface 111. Spiral 120 may have holes or slots near wick 118 and filled with the wicking material so that fluid can be transported radially outward in addition to the spiral path.

Before describing the remaining elements of the injecting means which is activated by hydraulic control, the underlying control system upstream from the injecting means 130 will first be described.

Figure 6:
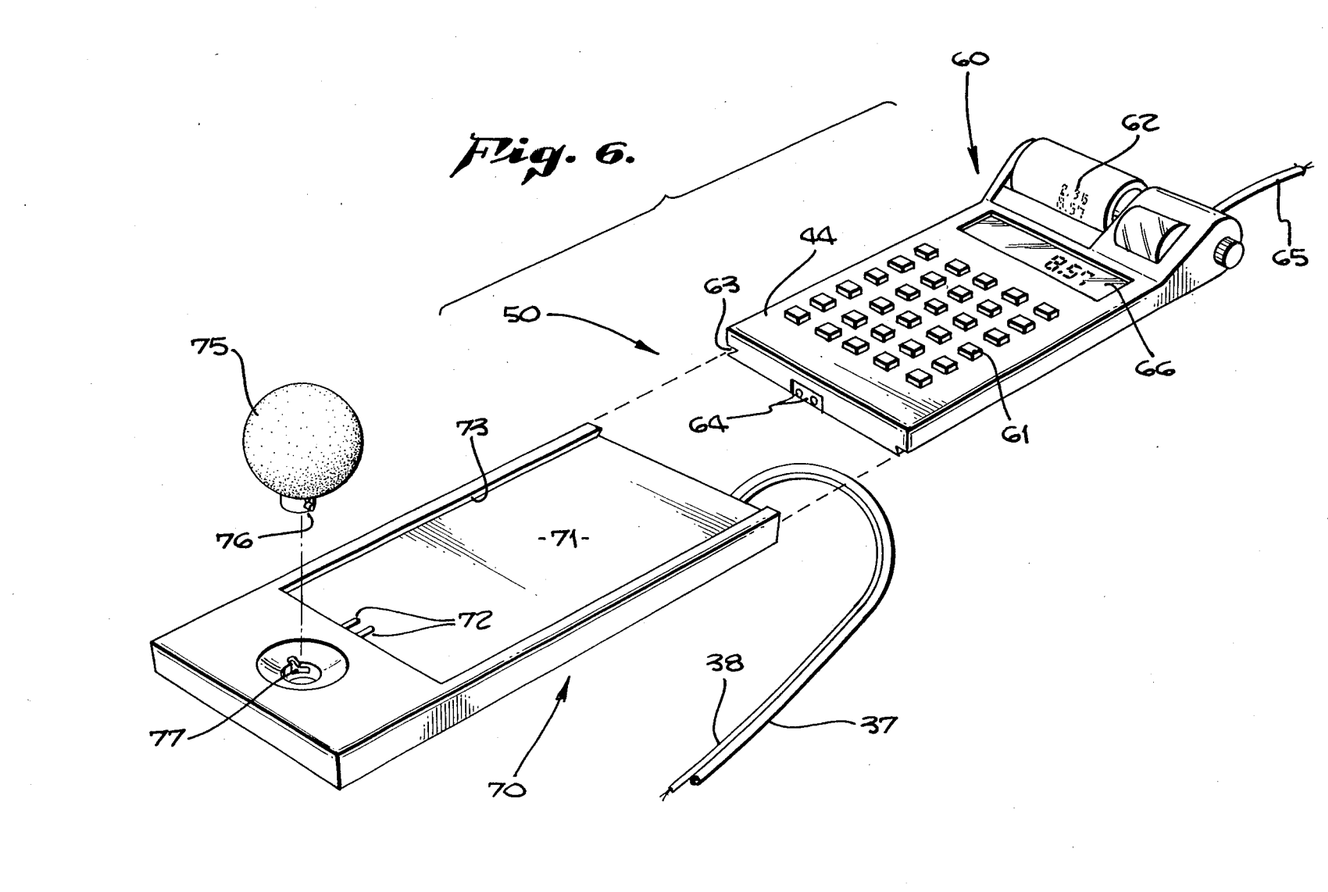
FIG. 6 is an exploded view in perspective of the portion of the apparatus of the present invention that controls the application of cold to the heat exchanger on the patient's skin and monitors temperature changes.
Figure 7:
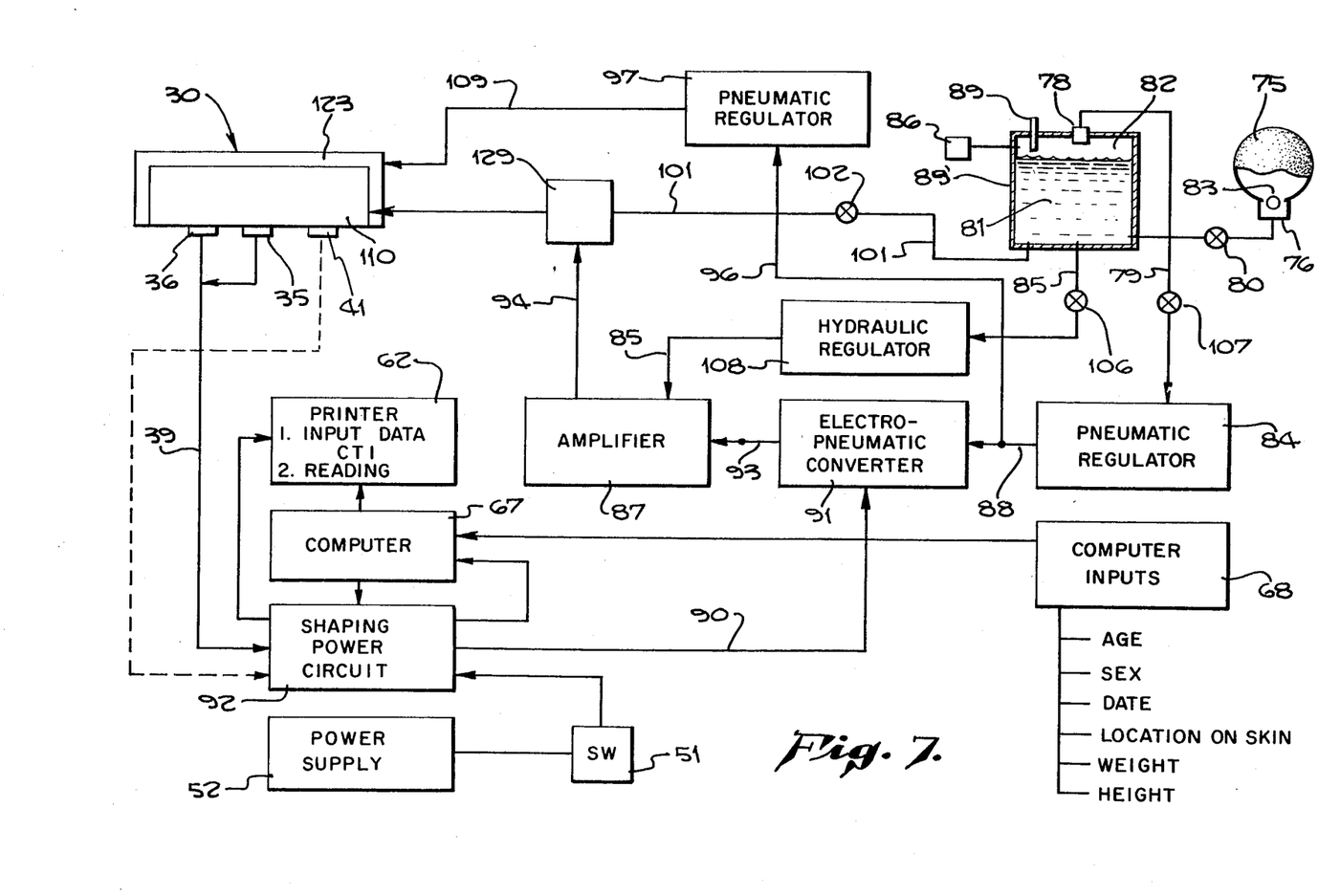
FIG. 7 is a block diagram illustrating the inventive system which performs the method of the present invention. Some of the elements in the block diagram are shown in somewhat physical detail.

Energy to operate the various valves necessary for controlling cooling is obtained from the pressurized fluid in chamber 75 (FIGS. 6 and 7). Chamber 75 is filled with the Freon mixture under pressure so that it is in liquid form. Chamber 75 may be disposable and is approximately the size of a golf ball, or 1-2 inches (3-5 cm) in diameter. At the bottom of chamber 75 is a male bayonet fitting 76 that mates with a female receiving member 77 in base 70. A valve 89 in the male member 76 and a valve 80 downstream from the female receiving opening 77 in the base prevent liquid from flowing out of the chamber 75 and base 70. These valves could operate together so that both would only open if the male member 76 of chamber 75 is properly inserted in the female receiving member 77. A secondary opening in chamber 75 or valve 76 may be used for filling the chamber 75.

It is desirable that the liquid phase flows out of chamber or tank 75 for reasons that will be evident. In that regard, a leveling sensor 86 (FIG. 7), which is known in the art, is permanently mounted on the base in any desired location (it is shown attached to tank 83 in FIG. 7) to give an audible or other warning or provide a signal to close valve 80 if base 70 is not level sufficiently while chamber 75 is mounted on the base 70. Alternatively, the control system could shut valves 102, 106 or 107 in any combination if base 70 is not relatively horizontal.

Liquid from tank 75 then flows past valve 80 into secondary or internal tank 83, and the tank is filled. A vent 89 may be provided to allow gas at the top of tank 83 to escape to atmosphere during filling. Such vents are well known, and they may be finger actuated to open. Escape of liquid indicates that tank 83 is filled. The operator would thereafter stop opening vent 89 as soon as liquid was discharged from it. The bottom of vent 89 should extend downward slightly below gas outlet 78 to provide a reservoir 82 of gas. It can be seen that there are a number of lines with appropriate valves leading from tank 83 as well as a vent and a gas outlet. These could be provided in chamber 75, but that would complicate the chamber. As chambers 75 may be disposable, it would be undesirable to further complicate them. Therefore, the intermediate tank 83 can accomplish all of the functions of a more complicated tank 75. Each cycle therefore costs less. Other ways of utilizing both the gas and liquid and controlling them could also be provided for.

The inside of tank 83 is shown in FIG. 7. Although it is shown rectangular, the shape can be modified. There it can be seen that the fluid divides itself into a liquid phase 81 and a gaseous or vapor phase 82. The fluid is a mixture of Freon fluorocarbons having particular vaporization characteristics and having safe breathing characteristics during venting and normal operation. The mixture is chosen such that the boiling point of the gas will cool heat exchanger surface 111 (FIG. 3) to a chosen temperature at a chosen rate. The mixture will boil below normal skin temperature but will boil above 32° F. (0° C.) so that frostbite will not occur.

One outlet 78 of tank 83 (FIG. 7) is located at the top of the tank so that only gas is discharged, and the gas passes through line 79 to valve 107 into pneumatic regulator 84. The minature pneumatic regulator lowers the pressure to a predetermined regulated pressure. The pressure in line 79 may vary with temperature of the fluid, and it is desirable to use a regulated pressure for controlling. Hydraulic line 85, which is valved at 106 carries liquid that is reduced in pressure at hydraulic regulator 108 to one input of amplifier 87.

The low pressure gas from regulator 84 is directed through line 88 into electro-pneumatic converter 91. The electro-pneumatic converter is actuated by an electrical signal through line 90 from shaping power circuit 92. Circuit 92 converts the analog signal from the sensors such as thermistors 35 and 36 from line 39 to a useable signal.

When a cooling cycle is to begin, circuit 92 signals electro-pneumatic converter 91 to permit gas to flow through line 93 into pneumatic amplifier 87. By using low pressure gas in the electro-pneumatic converter 91, only a small valve is needed therein. Thus, only a small amount of power in line 90 is needed to open the electro-magnetic converter. Utilizing higher pressure gas or liquid would require more of a power drain. When electro-pneumatic converter 91 opens, gas flows through line 93 into an input in fluid amplifier 87. Fluid amplifiers are well known. Some are discussed in *Tool Engineers Handbook,* 2d at 12-15 et seq. (1959). As will be discussed hereinafter, a hydraulic amplifier will be discussed in detail in FIG. 3. When electro-pneumatic converter 91 opens and gas flows through line 93, amplifier 87 injects hydraulic fluid from line 85 into line 94 at a higher pressure, if desired.

Cuff 30 (FIG. 3) shows a ballonet about the heat exchanger. Of course, heat transfer surface 111 is still exposed to the skin, but the ballonet 123 comprises a bellows wall 124 and a somewhat flexible top wall 125. Cuff 30 is loosely attached to the skin using straps 126. A portion of the gas, bled from line 88, is directed through line 96 to a pneumatic regulator 97, which can either be mounted in the base, or it can be at or near the cuff 30. Low pressure gas from pneumatic regulator 97 is then directed through line 109 into ballonet 123 (FIG. 7). By a predetermined regulation, the pressure in ballonet 123 applies a correct pressure of surface 111 to the skin. If the pressure is too great, the cuff will interfere with circulation and affect readings. Surface 111 and the sensors 35, 36 and 41 should be in contact with the skin. A gauge pressure of between 0.25 and 0.5 psi in the ballonet is considered desirable from test data.

Liquid 81 in tank 83 also flows into line 101 (FIG. 7) where it is controlled by valve 102. Valves 102 and 106 could be combined with line 85 being connected to line 101 downstream of valve 102, or line 101 could be connected to line 85 downstream from valve 106. Relatively high pressure liquid enters injector system 129 (FIGS. 3 and 7) from line 101, and a lower pressure fluid enters through line 94.

As shown in FIG. 3, injector system 129 is located within cuff 30, but it could be outside the cuff (see FIG. 7). Although lines 94, 101 and 109 are shown separately, it would be desirable if all entered the cuff through one inlet. Flexible, small diameter tubing with three or more attached tubes is available, and even the electrical leads from sensors 35, 36 and 41 may be attached to the tubes in spaces between them. Preferably, they would all enter the cuff through bellows wall 124 near the skin surface so as not to apply a torque to the cuff and the heat exchanger (FIGS. 2 and 3).

High pressure liquid in line 101 (FIG. 3) enters upper chamber 134 where it flows past check valve 135, which is urged against orifice 136 by spring 137, into main chamber or cell 138 of injector 130. Chamber 138 is formed in part of piston wall 139 which is flexible to allow top wall 140 and upper chamber wall 141 to move up and down in response to pressurization of chambers 138 and 145. The spring constants of springs 137 and 133 for check valves 135 and 132 are chosen such that normal maximum pressure in line 101 is sufficient to overcome spring 137 and allow liquid to flow past check valve 135 into main chamber 138, but the pressure is insufficient to overcome the force of spring 133 acting on check valve 132. Therefore, the high pressure liquid is contained within chamber 138.

The lower pressure liquid through line 94 is fed into control chamber or cell 145 (FIG. 3), which consists of top wall 146 and sidewall 147. Bottom wall 148 is mounted to wall 147 by flexible member 149 which permits bottom wall 148 to move up and down between lower ring stop 150 and upper ring stop 151. Upper chamber 134 and top wall 140 of injector 130 are connected to bottom wall 148. Spring 143 and pressure inside of chamber 138 urges bottom wall 148 upward against stop 151.

When fluid is injected through line 94, the pressure will exert a downward force on bottom wall 148. Because the area of bottom wall 148 is very much greater than the area of wall 140 of the main chamber 138, lower pressure in chamber 145 is amplified to force top wall 140 and top chamber 141 downward against the pressure in chamber 138 acting on wall 140. Bottom wall 148 moves down until it contacts bottom ring stop 150. This action greatly pressurizes the inside of main chamber 138 which overcomes the spring force of spring 132 and allows the liquid to be injected through orifice 131 into chamber 110. The check valve 135 prevents the higher pressure liquid from flowing back into line 101.

Thereafter, the pressure in line 94 is vented, and new liquid flows through lihe 101 past orifice 136 into main chamber 138 which creates an upward force in conjunction with spring 143 on wall 148 to allow main chamber 138 to fill again.

The above described injecting system 129 injects a precise amount of the liquid into cooling chamber 110. Minimum power is utilized, and the working fluids, which are maintained under pressure, do the work. Neither large electrical power or high voltage requirements are necessary, and the system is very compact. Also, by utilizing a liquid working fluid close to the heat exchanger, time lags are substantially reduced or eliminated, and the computing system does not have to compensate for such lags. Moreover, changes in outside temperature will have less affect.

In every instance, only liquid, not gas, is injected to heat exchanger surface 111. No latent heat of vaporization will occur except where it is wanted on surface 111. The vaporized liquid is vented as gas out of vent 153 (FIGS. 3 and 4).

Referring again to FIG. 5, the initiation of the cooling cycle is shown as points 3A, 3B, 3C and 3D on curve 1 and for curve 2, cooling starts at points 4A, 4B, 4C, and 4D. Although curves 1 and 2 assume a long test with approximately 6° F. (3° C.) temperature changes, the control system is accurate enough to permit smaller changes in temperature to decrease test time. The control system stops cooling when the temperature of the skin or heat exchanger reaches a predetermined point or after a predetermined interval. In one test, the designed heat exchanger cooled at approximately 3.1° F. (1.7° C.) per second so that a temperature drop of approximately 30° F. (17° C.) occurs in approximately ten seconds. The shutoff points along curve 1 are indicated as points 5A, 5B, 5C, and 5D and the shutoff points for curve 2 are indicated as 6A, 6B, 6C and 6D.

Once the heat exchanger starts cooling, the body works to maintain and return the skin temperature to its normal state. As stated before, the rate at which the skin temperature drops and the rate at which it returns to normal is correlated to the efficiency of the peripheral vascular system. Skin temperature of one with an inefficient vascular system will drop more quickly than that of a normal person. The efficient system may not drop as far, and it will return to normal more quickly.

In one test, after the skin reaches its normal or slightly below normal temperature at points 3, 4, etc., the cooling is again initiated. The body returns the area to normal more slowly on later cycles. As shown in FIG. 5, it takes longer for the healthy person's skin temperature to return to normal on the second cycle (point 5B to point 3C) than it does on the first cycle (point 5A to point 3B). The person with some disease, however, not only takes longer to return to a normal skin temperature after the first cycle (from 6A to 4B), but the rate of return to normal temperature slows to an even greater degree during subsequent cycles.

The device can plot temperature curves that trained persons can then read and diagnose conditions much like a physician reading an electrocardiogram or other graph of bodily functions.

Another method for analyzing the data would be to compare the curves mathematically to derive a numerical indicator. Because of the change in rates of return of skin temperature to normal between different subjects, the area under those curves can be determined by integration. The simplest way to integrate the curves is through computer analysis. This generates an index which will be called the cardio-thermal index or CTI. A CTI may be defined, for example, as the summation of the integrals of the temperature recovery portion of the curve over a given number of cycles divided by the summation of the integrals of the cooling portion. The result is non-dimensional, and the computer can express the result as a digital number or percentage of normal. The equation is thus:

$$CTI = \frac{\left\{ \Sigma_c \int_{n-1}^{n} T(t)dt \right\}_c}{\left\{ \Sigma_w \int_{n-1}^{n} T(t)dt \right\}_w}$$

where dt is the time differential; $T(t)$=skin temperature variation as a function of time, t, and temperature, T. The term $\Sigma_c$ is to be a summation of all forced cooling integrals to be considered from the first curve through a given number of curves, which will be odd. Referring to FIG. 5, the odd cycles are the cooling ones and include the first cycle (3A to 5A), the third cycle (3B to 5B), etc. Each curve is integrated. The term $\Sigma_w$ is a summation of all warming integrals being considered from the second curve through a given even number of curves, which is one larger than the given number during cooling. In FIG. 5, the even cycles are warming cycles and include the second cycle (5A to 3B), the fourth cycle (5B to 3C), etc. Each of those curves is integrated. It has been discovered that the resulting CTI is very sensitive to blood flow in the capillary bed.

It is believed that the temperature cycling causes the constriction and dilation of the arterioles to respond less efficiently during each succeeding cycle (similar to muscle fatigue after strenuous work). The effect is more pronounced with PVD. In short, there are two effects—(1) a single cycle effect that primarily shows blood flow rate in the capillary bed; and (2) a frequency damping effect, indicating the tone or normalcy of the arterioles.

Both effects can be examined, separated and manipulated by desired mathematical analysis and displayed by standard computer technology. Computer analysis obviates difficulties in visual analysis of complex analog data. By producing a numerical result or series of numbers, the system produces a more easily used and more informative result.

The testing and data interpretation of the present invention can be done in many other ways, for example:

(a) Applying cooling at a fixed rate for a specific time. This will yield a fixed rate of heat removal from the skin in the covered area for the specified time. The index from such a test could be correlated on the basis of either an average time/temperature slope, the maximum cooling rate, or an integral of the time temperature curve over some specified time or temperature range;

(b) Maintain the heat exchanger temperature for a specified period of time. Constant patch temperature cooling could be correlated in the same manner as constant cooling rate data;

(c) Applying cooling in a cyclic manner to generate a skin temperature excursion over a specified range. Data generated through cyclical heat removal may be correlated by plotting temperature recovery between cooling cycles versus the number of cooling cycles then by integrating this curve over the number of cycles generated; and (d) Applying cooling cyclically at a fixed cooling rate but varying the on/off cycles over different frequencies.

One of ordinary skill in the art can program the present system to operate in any of these manners by means of software for operating the system.

Referring again to the control and monitoring system of the present invention (FIGS. 6 and 7), monitor 50 (FIG. 6) has two main parts, a console 60 and a base 70. Console 60 includes a keyboard 61 that is used to program the conrol system. The keyboard may control the on/off function, or a separate switch 51 (FIG. 7) may control the electrical battery power supply 52. Keyboard 61 also inputs at 68 in FIG. 7 different variables such as height, weight, age, sex and location on the skin that the cuff 30 is placed. The keyboard 61 could also be used to enter the patient and physician's name, the date and time of the test and other related information so that the printer 62 (FIGS. 6 and 7), which is a standard calculator printer, can print this data for record keeping purposes. The keyboard 61 is tied into computer 67 (FIG. 7) that monitors and controls the controller. The computer 67 would include a preprogrammed ROM for the basic system controls and for the computation mathematics.

The console 60 mates with base 70 in the dovetailing grooves 63 and 73 on console 60 and base 70, respectively, which holds the two units together. A lock may be provided to prevent separation of the base 70 from the console 60. When grooves 73 and 63 engage each other and console 60 is pushed entirely within receiving opening 71 of the base 70, male electrical connector 72 will engage corresponding female electrical members 64 on the console 60. Sensed data from the temperature sensors in the cuff 30, transmitted through wires in cable 38 (FIGS. 6 and 7) to console 70 is thereafter transmitted through electrical connectors 72 and 64 (FIG. 6) to console 60.

In addition to the printer 62 for printing an alphanumerical CTI, the console could be connected through output line 65 (FIG. 6) to a graphic printer where the analog results of the tests are printed and/or to a remote monitoring station in which either analog or digital results could be displayed, for example, at a hospital nursing station. In addition to the printout 62, the console 60 may also have a digital display 66 for instantaneous monitoring of the CTI.

It is advantageous to minimize the electrical power requirements especially the power to cuff 30. Therefore, most of the cooling control is done hydraulically or pneumatically as shown above. The power requirements for the small computer housed within console 60 are small enough for small battery power. The temperature sensors on the cuff 30 are thermistors 35 and 36 (FIG. 3). Thermistors respond to temperature changes by changes in resistance. A small voltage across the thermistors 36 or 36 is sufficient to read the temperature change. Because of insulation 39 between sensor 35 and the skin, sensor 35 reads the temperature of surface 111; sensor 36 reads skin temperature because of insulation 40 between the sensor and the surface 111. Utilizing a small voltage for a temperature sensor is important for safety reasons; large voltage near the skin is undesirable if there is a short. All of the small batteries that could be used to power the computer in console 60 pose no danger to the patient. A platinum resistance thermistor (PRT) is desirable because of its linearity, but the computer could compensate for nonlinearity. A sensor 41 for measuring heat flux could also be provided for additional data.

It will be recognized that the injecting system may have other applications, and a number of other components have other uses. The diagnostic method also can be altered. The exemplary embodiment of the present invention has been described. It will be recognized that many modifications are possible, and the exemplary embodiment is not intended to be a limitation on the invention.

I claim:

1. A method for monitoring blood flow comprising applying an object of a temperature below normal skin temperature to the surface of an area of skin to lower the temperature of the area of skin;

terminating the application of the object at a temperature below normal skin temperature whereby internal blood flow around the area of skin raises the temperature of the area of skin; and monitoring the temperature within the area of the skin as the temperature changes in response to the application of the object at a temperature below normal skin temperature and as it returns to its original temperature when the application of the object at a temperature below normal skin temperature is terminated.

2. The method of claim 1 further comprising comparing the skin temperature changes to a predetermined normal change in skin temperature for the area of skin.

3. The method of claim 1 further comprising repeating the steps of application of the object and of termination of application of the object to the area of skin and continuing the monitoring of the temperature of the area of skin.

4. The method of claim 1 further comprising devising a numerical index from the results of the monitoring including integrating the rate of change of temperature of the area of skin per unit time during the time in which the object is being applied to the skin, dividing that result by the integral of the rate of change of the temperature of the area of skin for at least one cycle of application and termination of application of the object.

5. The method of claim 1 further comprising the step of applying a heat exchanger to the area of skin, and varying the temperature of the heat exchanger at a fixed rate for a predetermined time.

6. The method of claim 5 further comprising the step of determining the average rate of change of temperature of the area of skin per unit time.

7. The method of claim 5 further comprising determining the maximum temperature change to the area of skin during the time period.

8. The method of claim 5 further comprising the step of mathematically integrating the change in temperature of the area of skin over time for a specific time period.

9. The method of claim 5 further comprising mathematically integrating the temperature of the area of skin over time for a specific temperature range.

10. The method of claim 1 wherein the step of applying an object to the skin is accomplished by placing a heat exchanger on the skin, the heat exchanger being maintained at a constant temperature for a predetermined length of time.

11. The method of claim 1 wherein the object is applied again a predetermined time after the skin begins returning to its original temperature because of termination of application, the method further comprising the step of modifying the predetermined time for initiating again the application of the object to the skin.

12. The method of claim 1 wherein the object applied to the skin is a heat exchanger, the heat exchanger cooling by injecting into the heat exchanger a liquid having a boiling point lower than skin temperature, the heat generated by normal skin temperature boiling the liquid to cool the heat exchanger and the skin.

13. A method for monitoring blood flow comprising:
artificially cooling an area of skin by applying an object to the skin, the object being at a temperature below normal skin temperature:
monitoring the rate of change of the skin temperature as it changes in response to the application of the object; and
comparing the rate of change of the skin temperature to a predetermined normal rate of change in skin temperature for the area of skin.

14. A method for monitoring blood flow comprising:
artificially changing the temperature of an area of skin by applying an object to the skin for a period of time, the object being at a temperature below normal skin temperature; and
monitoring the skin temperature as it returns to the original temperature after the period of time; and
comparing the rate of change for the skin temperature to a predetermined normal rate of change in skin temperature for the area of skin.

15. A heat exchanger apparatus for cooling an object comprising:
a cooling chamber, one side of the chamber being surface means having two faces, a first face being adjacent to the object for contacting the object;
injecting means connected to a source of fluid, the fluid having a boiling point at ambient pressure less than the temperature to which the object is to be cooled, the injecting means injecting fluid into the chamber and onto the face of the surface means opposite first face and the object to boil the fluid on the surface means to cool the surface and the object.

16. The heat exchanger of claim 15 further comprising wick means on the surface means in the chamber for distributing the fluid along the surface means.

17. The heat exchanger of claim 15 further comprising guide means on the surface means for guiding the fluid from the injecting means to spaced apart locations on the surface means.

18. The heat exchanger of claim 17 wherein the guide means comprises a spiral wall upstanding from the surface means.

19. The heat exchanger of claim 17 further comprising secondary wick means adjacent the injecting means and in contact with the surface means and the guide means for moving fluid not on the surface means to the surface means.

20. The heat exchanger of claim 15 wherein the injecting means comprises dividing means for dividing fluid flow from the source of fluid into two flow paths, first pressure reduction means in one flow path for reducing the pressure in the flow path to a lower pressure, first cell means connected to the first pressure reduction means for receiving the lower pressure fluid flow from the pressure reduction means, the first cell means having a first wall movable in response to pressurized fluid from the pressure reduction means, second cell means connected to the dividing means for receiving higher pressure fluid flow from the second flow path, the second cell means having a second wall having an area less than the area of the first wall, the second wall being movable in response to movement of the first wall to change the volume of the second cell means, the second cell means having an opening to the chamber through which fluid can flow, first check valve means in the second cell means across the opening and being normally closed for blocking fluid flow through the opening when the fluid in the second cell means is at its normal, higher pressure, the first check valve means opening when movement of the second wall decreases the volume of the second cell means to inject fluid through the opening into the chamber.

21. The heat exchanger of claim 20 further comprising first stop means on one side of the first wall for limiting travel of the first wall in a direction to decrease the volume of the first cell means to limit the maximum volume of the second cell means, second stop means on the other side of the first wall to limit travel of the first wall in an opposite direction to limit the minimum volume of the second cell means for precise volume change to control the amount of fluid injected into the chamber.

22. The heat exchanger of claim 21 further comprising governing means between the source of fluid and the first cell means for initiating flow of fluid into the first cell means and stopping flow of fluid into the first cell means.

23. The heat exchanger of claim 22 further comprising sensing means adjacent the object for sensing the temperature of the object, and feedback means between the sensing means and the electrical valve means for controlling the electrical valve means in response to changes in temperature sensed by the sensing means.

24. The heat exchanger of claim 21 further comprising resilient means attached to the first wall for urging the first wall toward the first stop means and moving the first wall toward the first stop means when the governing means stops the flow of fluid into the first cell means to lower the fluid pressure therein.

25. The heat exchanger of claim 20 further comprising inlet means into the second cell means through which higher pressure fluid from the source of fluid flows into the second cell means, second check valve means at the inlet means for permitting one way flow of fluid through the inlet means.

26. The heat exchanger of claim 25 further comprising the first check valve means having first spring means for urging the first check valve means closed, the second check valve means having a second spring means for urging the second check value means closed, the spring constant of the first spring means permitting the first check valve means to open under greater pressure than the second spring means permits the second check valve means to open.

27. The heat exchanger of claim 20 further comprising a secondary outlet means from the source of fluid for directing a controller fluid therethrough, second pressure reduction means downstream from the secondary outlet means for reducing the pressure of the controller fluid from the pressure of the source of fluid, electrical valve means in the path of the controller fluid opening and closing in response to a signal from a regulator circuit, amplifier means downstream from the electrical valve means for receiving the controller fluid when the electrical valve means is open and for receiving the lower pressure fluid flows from the first pressure reduction means for controlling the flow of the lower pressure fluid in response to changes in the flow of the controller fluid from the electrical valve means.

28. The heat exchanger of claim 27 wherein the source of fluid has an upper and a lower portion and contains liquid and gas under pressure, the secondary outlet means being positioned in the upper portion of the source of fluid such that the controller fluid is a gas and a primary outlet from the source of fluid upstream of the dividing means and positioned in the lower portion of the source of fluid such that the fluid directed to the dividing means is liquid.

29. The heat exchanger of claim 27 further comprising sensing means adjacent the object for sensing the temperature of the heat exchanger, and feedback means between the sensing means and the electrical valve means for controlling the electrical valve means in response to changes in temperature sensed by the sensing means.

30. The heat exchanger of claim 27 further comprising heat flux sensing means adjacent the object for sensing the heat flux from the object to the heat exchanger, and feedback means between the sensing means and the electrical valve means for controlling the electrical valve means in response to changes in heat flux sensed by the sensing means.

31. The heat exchanger of claim 20 further comprising a ballonet about the heat exchanger, ballonet opening means through a portion of the ballonet for exposing the surface means there through, attaching means on the ballonet for loosely attaching the ballonet to the object, filling means attached to the ballonet for filing the ballonet with low pressure gas to urge the ballonet and the surface means of the heat exchanger against the object at a controlled pressure.

32. The heat exchanger of claim 28 wherein the source of fluid contains liquid and gas under pressure, the secondary outlet means being positioned in the upper portion of the source of fluid such that the controller fluid is a gas, dividing means for directing a portion of the gas into a filling conduit, pressure lowering means in the filling conduit for lowering the pressure to a controlled level in the conduit and connection means for connecting the filling means to the ballonet.

33. A system for monitoring blood flow comprising:
heat exchanger means for changing the temperature of an area of skin in a controlled manner, the heat exchanger means having a cooling surface, a source of fluid having liquid and vapor phases under pressure, the liquid having a boiling point less than skin temperature at atmospheric pressure, controlling means for controlling injection of the liquid into the heat exchanger means whereby the skin temperature heating the heat exchanger means boils the liquid to cool the heat exchanger means thereby cooling the skin,
cuff means attached to the heat exchanger means for attaching the heat exchanger means to the skin;
monitoring means attached to the cuff means and mounted adjacent to the skin for monitoring he skin temperature as it changes in response to changes in the temperature of the heat exchanger means.

34. The system of claim 33 further comprising dividing means attached to the source of fluid to divide the fluid flow into a main flow in a main line and a control flow in a control line, secondary dividing means downstream of the dividing means for dividing the control flow into a high pressure flow in a high pressure line and a lower pressure flow in a lower pressure line, low pressure valve means in the lower pressure line downstream from the secondary dividing means for regulating flow through the lower pressure line in response to a signal from a controlling circuit, amplifier means having an input from the lower pressure line downstream from the low pressure valve means and having a second input from the high pressure line, a main valve having an input from the amplifier means, a second input from the dividing means and an outlet in the heat exchanger means, the main valve opening in response to flow of the high pressure flow from the amplifier means in response to flow of the lower pressure flow from the low pressure valve means to the amplifier means for opening the main valve and permitting flow of fluid from the source of fluid past the main valve into the heat exchanger.

35. A system for measuring the level of peripheral blood flow comprising:
temperature changing means adapted to be attached to the skin for changing the temperature of the skin,
monitoring means adapted to be attached to the skin adjacent the temperature changing means for monitoring change in skin temperature caused by the temperature changing means,
control means operatively associated with the temperature changing means for selectively operating the temperature changing means through at least two cycles, during each cycle, the temperature changing means changing the skin temperature to a predetermined temperature then permitting the skin temperature to approach normal.

36. A system for measuring the level of peripheral blood flow comprising:

temperature changing means adapted to be attached to the skin for changing the temperature of the skin, control means for selectively operating the temperature changing means through at least two cycles, during each cycle, the temperature changing means changing the skin temperature for a predetermined time then permitting the skin temperature to approach normal.

* * * * *